US006628746B2

(12) United States Patent
Eppler et al.

(10) Patent No.: US 6,628,746 B2
(45) Date of Patent: Sep. 30, 2003

(54) IMAGE-BASED INSPECTION SYSTEM INCLUDING POSITIONING COMPENSATION FOR NON-PLANAR TARGETS

(75) Inventors: Barry Eppler, Loveland, CO (US); Ronald K Kerschner, Loveland, CO (US); Martin C. Shipley, Fort Collins, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/021,383

(22) Filed: Oct. 30, 2001

(65) Prior Publication Data

US 2003/0081717 A1 May 1, 2003

(51) Int. Cl.[7] .................................................. A61B 6/00
(52) U.S. Cl. ............................................ 378/21; 378/25
(58) Field of Search ........................... 378/20, 21, 23, 378/24, 25, 26; 250/370.09

(56) References Cited

U.S. PATENT DOCUMENTS 6,084,663 A * 7/2000 Seng ........................ 356/237.4
6,330,837 B1 * 12/2001 Charles et al. ........... 74/490.06

* cited by examiner

Primary Examiner—Edward J. Glick
Assistant Examiner—Courtney Thomas
(74) Attorney, Agent, or Firm—Kyle J. Way

(57) ABSTRACT

A image-based system for inspecting objects utilizes an imaging chain that defines a focal plane, a manipulator for translating and rotating either the object under inspection or the imaging chain, a surface mapping system that generates a representation of the surface of the object under inspection, and a controller that uses the representation of the surface of the object to control the manipulator so that a portion of the object under inspection lies within the focal plane of the imaging chain.

33 Claims, 6 Drawing Sheets

IMAGE-BASED INSPECTION SYSTEM INCLUDING POSITIONING COMPENSATION FOR NON-PLANAR TARGETS

BACKGROUND OF THE INVENTION

Today, image-based inspection systems are often employed for physical inspection of an object of interest. Such systems typically employ an optical- or x-ray-based source at a distance from an object of interest at which an area of the object is in focus. Additionally, many such systems currently employ a positioning mechanism whereby the distance between the imaging source and the object is adjustable so that the area of the object to be inspected may be brought into proper focus.

For example, x-ray laminography machines that are employed to inspect printed circuit boards (PCBs) for manufacturing defects often utilize such a mechanism to keep a portion of the board under inspection within a narrow focal plane. That focal plane represents a thin "slice" of the PCB under inspection, allowing a view of a limited depth within the PCB. Such a view provides an advantage over typical transmissive x-ray inspection systems, which do not employ a focal plane, thus providing a view of all components and interconnections simultaneously, making analysis of the physical aspects of the PCB difficult. The position of the focal plane is determined by the location of an x-ray source and x-ray detector, which reside on opposite sides of the PCB under inspection. The area under inspection at any one time, which is normally termed a field of view, is roughly square in shape, and is typically much smaller than the area of the PCB itself. Consequently, the PCB is viewed in increments, section by section, layer by layer, until all areas of interest are inspected.

Unfortunately, warping of the PCB may be of sufficient severity that some portion of an area being inspected at any one time may remain out of focus, forcing the use of an even smaller inspection area. As seen in FIG. 1, a warped PCB 100 may cause all but a small area on the top side of PCB 100 to reside outside of a depth of focus 110 of an optical or x-ray inspection system, resulting in a small area, defined by a narrow width 120, that may be inspected at any one time. The use of a reduced inspection area generally results in more inspection areas being necessary for each PCB, thereby resulting in a significantly longer inspection time required for each PCB and, consequently, a drastic reduction in PCB inspection throughput.

Additionally, the focus problems due to PCB warping can also cause the inspection system to falsely identify out-of-focus areas of the PCB under inspection as manufacturing defects, resulting in costs due to unnecessary additional testing or discarding of properly manufactured PCBs.

Such problems regarding a changing focal distance over the surface of an object are not limited to PCB x-ray laminography inspection machines. Other optical- or x-ray-based viewing or inspection machines that employ only a focal length adjustment likely encounter the same difficulties with objects having a nonplanar structure to be viewed or inspected.

Therefore, from the foregoing, a new image-based inspection system that allows more area of an object under inspection to reside within the depth of focus, thus allowing for a greater inspection area and, thus, higher inspection throughput, would be advantageous.

SUMMARY OF THE INVENTION

Embodiments of the invention, to be discussed in detail below, allow the relative position between an object under inspection and the focal plane of an image-based inspection system to be altered by way of translation and rotation so that more of the object will reside within the focal plane. Continuing with the PCB example in FIG. 2, if the warped PCB 100 (from FIG. 1), or the imaging source/detector pair, is translated and rotated in a certain way, more area of the top surface of PCB 100, as defined by larger width 200, lies within depth of focus 110. Since warping or other irregularities in an object under inspection can occur in any direction along a surface of the object, the ability of an image-based inspection system to translate and rotate either the object or the imaging system to properly align the object with the focal plane is desirable.

An image-based inspection system according to an embodiment of the invention includes, in part, means for imaging a portion of an object under inspection. As noted earlier, the imaging means provides a focal plane that allows the viewing of a figurative "slice" of the object. To allow more of an area of interest within the object to be viewed, means for altering the relative position of the focal plane of the imaging means and the object is provided. The positioning altering means manipulates the translational location and rotational orientation of the object or the imaging means. Also included is means for mapping part of the surface of the object, thereby generating a representation of that part of the surface of the object. A means for controlling the operation of the manipulating means then utilizes the surface representation so that the portion of the object being inspected lies substantially within the focal plane of the imaging means. Optionally, means for automatically interpreting the image from the imaging means is included.

Another embodiment of the invention exists in the form of a method of image-based inspection of an object, with a portion of the object to be inspected being required to lie within a focal plane in order to be imaged. First, at least part of the surface of the object is mapped so that a representation of that part of the surface of the object is generated. Next, the translational position and rotational orientation of either the object or the narrow focal plane is altered based on the surface representation so that the portion of the object being inspected lies within the focal plane. That portion of the object is then imaged for inspection purposes. Optionally, the resulting image may then be automatically interpreted to determine the status or quality of the object.

Other aspects and advantages of the invention will become apparent from the following detailed description, taken in conjunction with the accompanying drawings, illustrating by way of example the principles of the invention.

DETAILED DESCRIPTION OF THE PREFERRED EMBODIMENTS

The embodiments of the invention, which are described below, are contemplated as a result of development work involving an x-ray laminography PCB inspection system. However, other inspection systems, whether based on optics, infrared (IR) emissions, x-rays, gamma rays, ultraviolet (UV) radiation, or other image detection means, and employed for inspection of a variety of items, could utilize embodiments of the invention advantageously.

Also, the following embodiments herein disclosed assume that the focal plane of the system is oriented horizontally. While this arrangement is the most popular one employed in image-based PCB inspection systems, other orientations of such systems are contemplated within the scope of the following embodiments.

Figure 1:
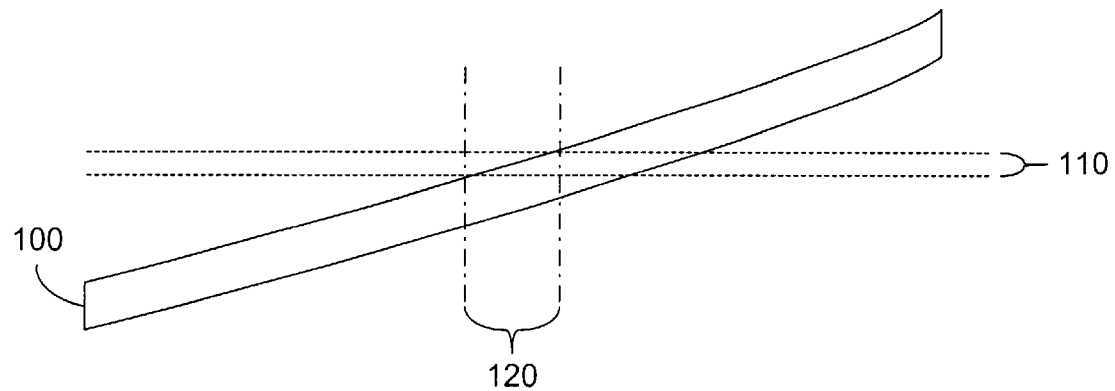
FIG. 1 is a diagram of a PCB that is warped to such an extent that the depth of focus associated with an image-based inspection system from the prior art allows only a small area of the PCB to be inspected at any one time.
Figure 2:
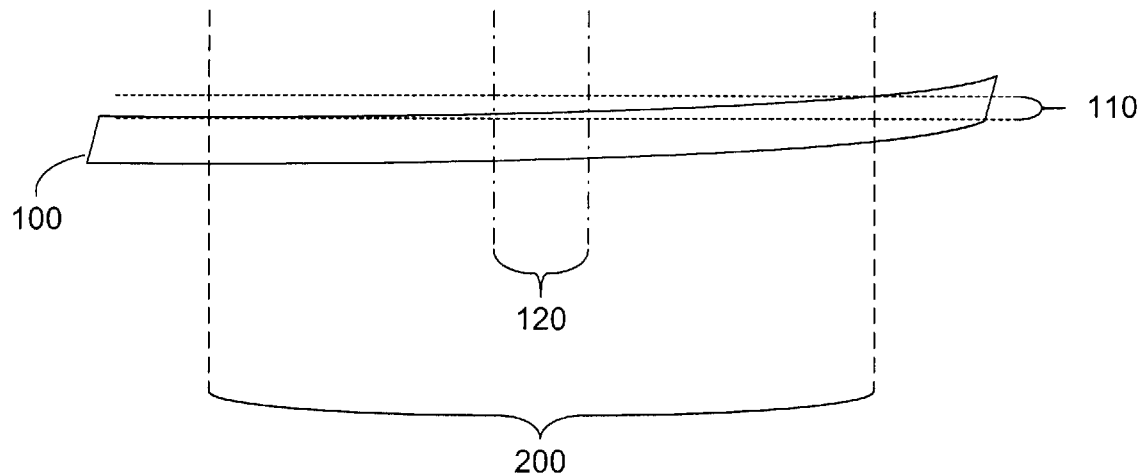
FIG. 2 is a diagram of the PCB from FIG. 1 that is rotated so that a larger area of the PCB may be inspected at one time by an image-based inspection system according to an embodiment of the invention.
Figure 3:
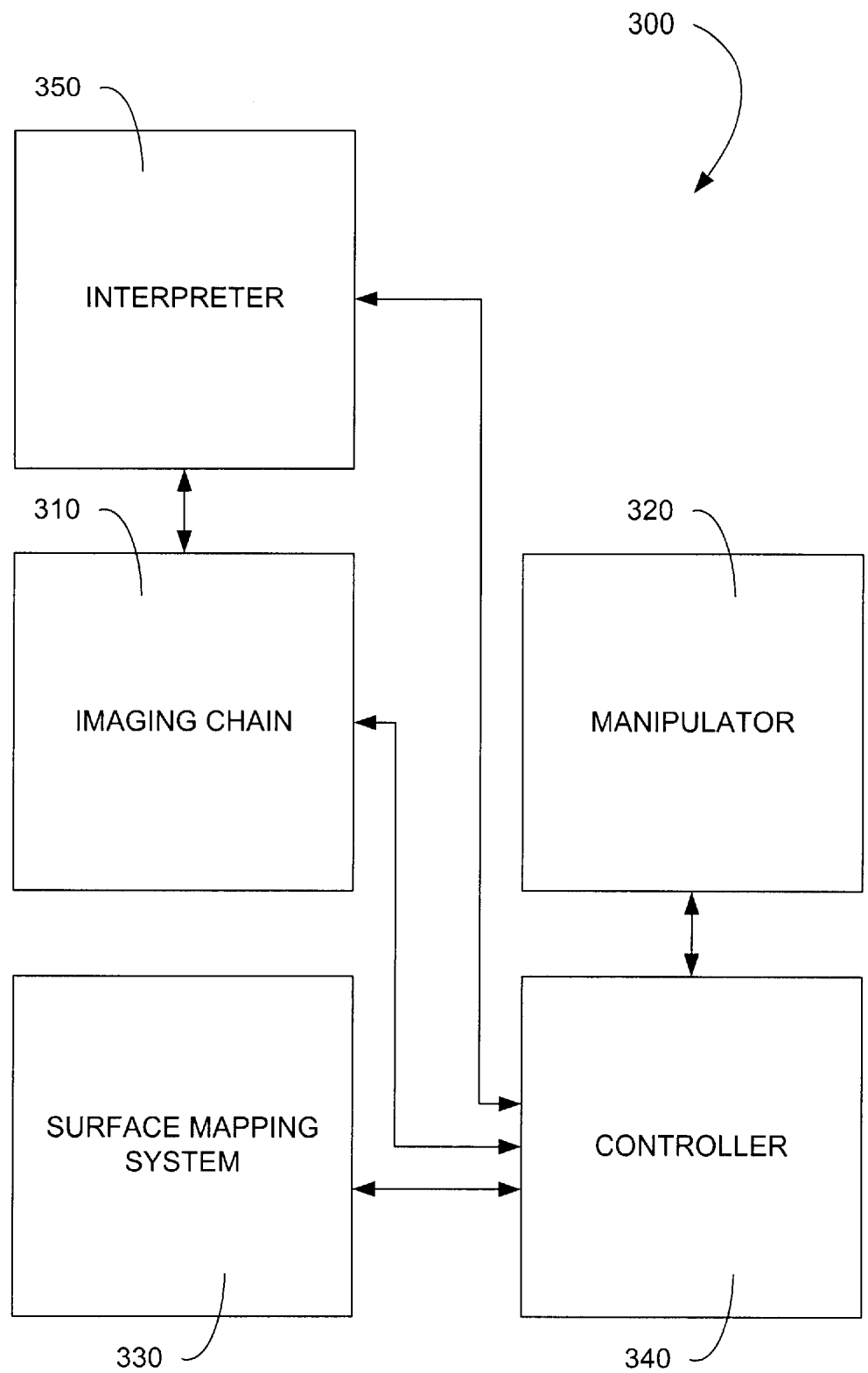
FIG. 3 is a block diagram of an image-based inspection system according to an embodiment of the invention.

An image-based inspection system 300 according to an embodiment of the invention is shown in FIG. 3. A major component of inspection system 300 is an imaging chain 310 that captures an image of a portion of an object under inspection. The portion being imaged is determined by a focal plane defined by the physical characteristics of imaging chain 310, which may be optical or x-ray-based in nature.

Several different types of x-ray-based imaging chains which are currently employed in inspection systems can be utilized for imaging chain 300. Two of the more popular are based on x-ray laminography and digital tomosynthesis, both of which are well-known in the art. X-ray laminography generally consists of a scanning x-ray source used in conjunction with an x-ray detector that captures multiple images of the x-rays from the source that are transmitted at various angles through an object to be inspected. The plane at which the various paths between the source and detector intersect is the focal plane determined by the imaging chain. The depth of focus of the imaging chain is determined by the distance between the source and detector, the angle of the line defined by the source and detector with respect to the focal plane, and other factors.

X-ray laminography imaging chains may scan the object involved in either a linear or rotary fashion. With respect to rotary scanning, many x-ray laminography imaging chains employ a rotary scanning x-ray tube as the x-ray source, and a rotary scintillator, which normally rotates in the same rate and direction as the scanning x-ray tube, but is positioned 180 degrees out of phase with the tube. An x-ray camera then continuously captures the images through the scintillator. As a result, the same general portion of the object under inspection is viewed by the camera from a constantly varying point of view. The portion of the object under inspection that remains stationary in view defines the focal plane. All other "layers" of the object move about within the field of view as a result of the tube and scintillator movement, causing the images of those layers to appear light or blurry compared to the images of the portion within the focal plane, thus allowing a focused view of only the portion of the object within the focal plane.

Digital tomosynthesis works using a similar principle of a moving x-ray source. However, several discrete images are captured by either a moving detector or several stationary detectors positioned along the path of the x-rays from the source that are transmitted through the object under inspection. The various discrete images are then combined digitally using a computer to generate an image of the portion of the object under inspection that lies within the focal plane of imaging chain 310.

Referring again to FIG. 3, a manipulator 320 is utilized to translate and rotate the object under inspection so that a portion of the object to be inspected will lie within the narrow focal plane of imaging chain 310. Use of such a manipulator is advantageous over a mechanism that only provides translational movement of the object, as rotational movement allows more of a portion of the object that is of interest to be oriented within the focal plane.

Figure 4:
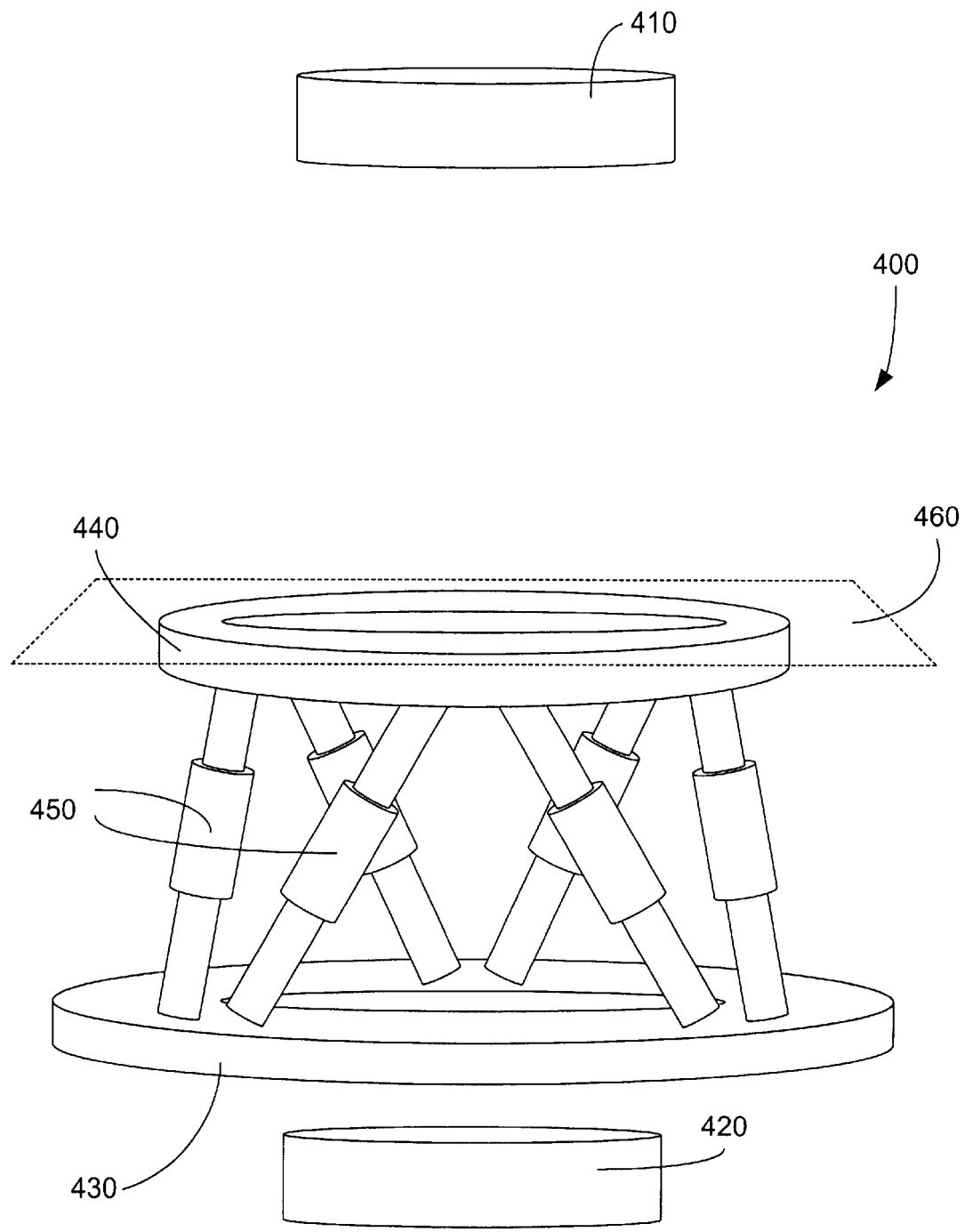
FIG. 4 is a perspective view of a hexapod that may be used as a manipulator in an image-based inspection system according to an embodiment of the invention.

Many different adjustment mechanisms from the prior art may be utilized as manipulator 320. For example, as shown in FIG. 4, a hexapod 400, which is also commonly known as a Stewart platform, may be utilized in various embodiments of the present invention. Hexapod 400 typically consists of a base 430, a retainer 440 that holds the object under inspection (not shown), and six actuators 450 that couple base 430 with retainer 440. Hexapod 400 is positioned so that the object held by retainer 440 may lie within a focal plane 460 defined by imaging chain 310, described in FIG. 4 by image source 410 and image detector 420. As is known from the prior art, actuators 450 can translate retainer 440, and hence the object under inspection, along any three orthogonal axes in three-dimensional space, as well as rotate retainer 440 about any of those axes, producing a full six degrees of freedom of movement. Translation movement parallel to focal plane 460 allows different portions of the object under inspection to be viewed by imaging chain 310, while translation perpendicular to focal plane 460 allows the portion of the object to be imaged to be brought into proper focus. The rotational movement allows the portion of the object of interest to be aligned with focal plane 460 so that more of the object may be imaged at any particular time. Other mechanisms that cause similar movement of the object under inspection may also be implemented for manipulator 320.

Additionally, other versions that provide fewer degrees of movement may be employed for manipulator 320. Specifically, a mechanism that provides translational movement in any direction, as well as rotational orientation about two of three orthogonal axes, could be implemented in embodiments of the invention. For example, a mechanism that is capable of any translational three-dimensional movement, as well as rotation about two orthogonal axes that are parallel to focal plane 460 of imaging chain 310, is sufficient for the purposes of embodiments of the present invention. Such rotation is able to compensate for warping and other anomalies of the object, such as in the case of a PCB. Alternately, a mechanism that provides three-dimensional translation, and allows rotation about an axis parallel to focal plane 460 and an axis perpendicular to focal plane 460, would also provide the rotational degrees of freedom necessary to the align a portion of the object to be inspected within focal plane 460. Additionally, if the nature of the object under inspection is such that any warp or other anomaly generally occurs in a specific direction, a mechanism that allows translation in all three directions, plus provides rotation about a single axis parallel to focal plane 460, may be sufficient for inspection of that type of object.

Furthermore, depending on the nature of the object under inspection, it may be possible to utilize a mechanism that only translates the object along an axis perpendicular to the focal plane, along with some rotating capacity. In this instance, the portion of object that is to be inspected would have to be sufficiently small so that the entire portion could fit within the field of view of imaging chain 310.

In other embodiments, imaging chain 310, as opposed to the object under inspection, may be translated and rotated by manipulator 320 so that the focal plane defined by imaging chain 310 aligns properly with the object, using the same embodiments for manipulator 320 described above. For example FIG. 4A shows such an embodiment, with a hexapod 400 manipulating both an image source 410 and an image detector 420, thus moving an associated focal plane 460 in relation to an object under inspection (not shown). Such embodiments are advantageous for objects that are best left in a stationary position, such as small, fragile objects, or large, immobile objects. Inspection of the human anatomy would also benefit from such an embodiment, as the human subject would most likely be more comfortable if left in a substantially stationary position.

Returning again to FIG. 3, the information required to determine how manipulator 320 must be operated is generated by a surface mapping system 330. The primary purpose of surface mapping system 330 is to generate a representation of at least part of the surface of the object under inspection in the portion of the object that is to be inspected. In other words, a "map" describing the topology or shape of the surface of the object is produced.

Figure 5:
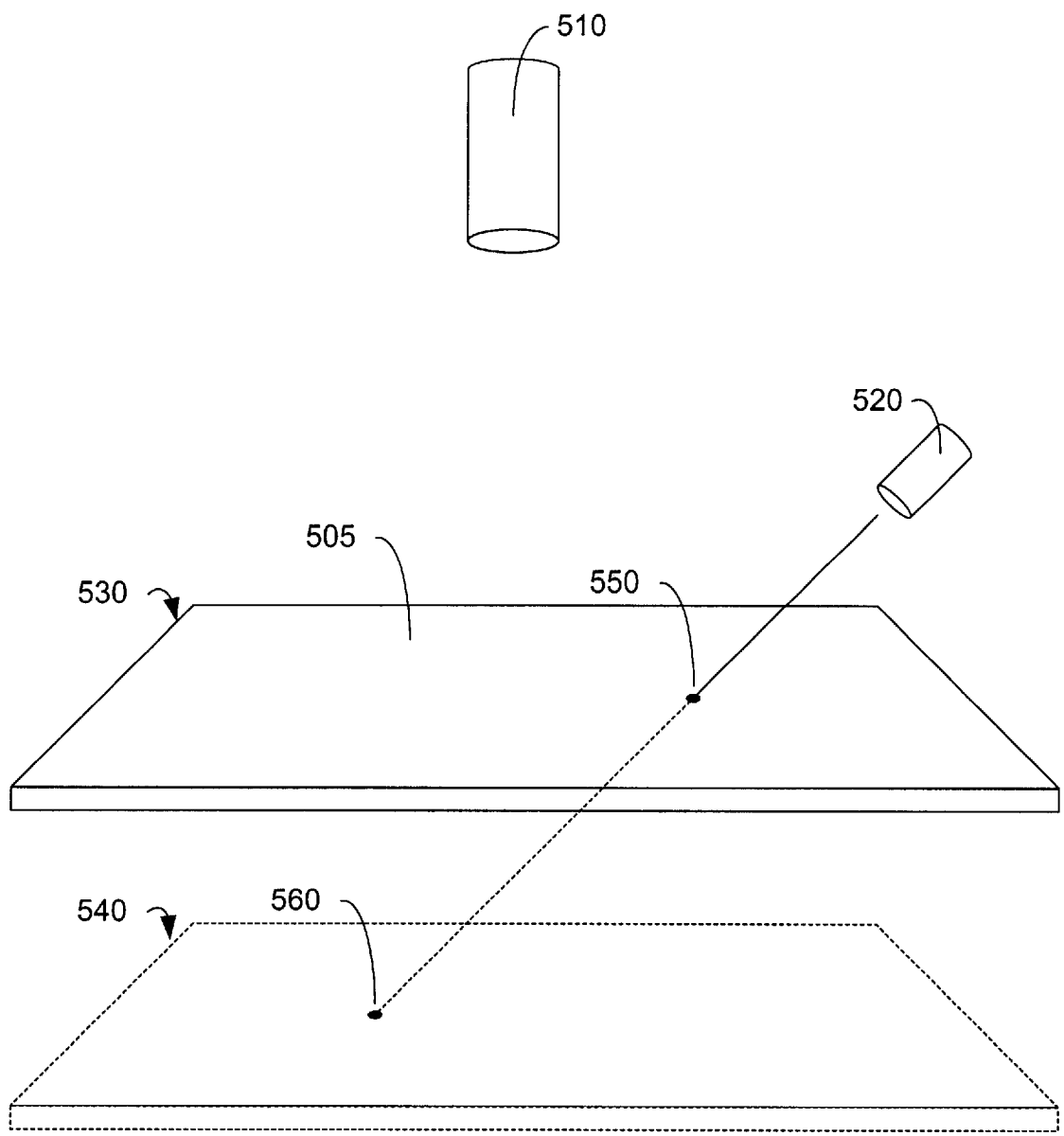
FIG. 5 is a simplified diagram of the operation of a laser distance sensor system that may be used as part of a surface mapping system in an image-based inspection system according to an embodiment of the invention.

Several methods of generating the surface representation of the object may be employed. For example, a laser distance sensor system from the prior art may be utilized for this purpose. As shown in FIG. 5, a laser light source 520 may be directed at an angle from a portion 505 of the surface of an object, which in this case is located at first vertical position 530. Laser light source 520 projects a first spot 550, which is detected by camera 510. The combination of the position of laser light source 520, the angle of the light from laser light source 520 with respect to camera 510, and the position of first spot 550 determine the height of the portion of the surface being illuminated. If portion 505 of the surface being mapped is instead located at second vertical position 540, a second spot 560, at a different position than that occupied by first spot 550, would be detected by a camera 510, thus indicating a different height of that portion of the surface being illuminated. Therefore, the position of the spot generated by laser light source 520 indicates the height for that portion of the surface of the object. Illuminating various points of the surface of the object under inspection allows the height of the various points on the object to be determined. Both the positioning of the laser light source 520, along with the calculations necessary to determine the height of each laser spot detected, may be performed with the aid of an algorithmic controller, such as a computer or microcontroller, programmed to perform the necessary calculations.

Surface mapping system 330 (of FIG. 3) may also be embodied as a photogrammetric system from the prior art. Generally speaking, one or more optical cameras, in conjunction with various light sources and optical sensors, are employed to view the surface of the object under inspection from at least two different angles. The resulting images from the cameras are then captured and processed by way of hardware or software to generate the surface representation required.

Additionally, the functionality of surface mapping system 330 may instead be provided by a focus mapping system. Under that system, an optical- or x-ray-based source and detector pair, or analogous structure, is used to view a portion of the surface of the object. The relative distance between the source/detector pair and the surface of the object is modified, possibly by operation of manipulator 320, until the portion of the surface being viewed lies within the focal plane of the source/detector pair. At that point, the relative height of that portion of the surface is known because the focal plane of the source-detector pair can be accurately determined. Continuing this process over all points of interest on the object under inspection thus allows the generation of the "map" required.

Surface mapping system 330 may also take the form of a physical probing system. In such a system, each point of interest to be measured is detected by a probe that makes contact with the point of interest on the object. The distance between the object and the probe is modified, possibly by movement of the object via manipulator 320, until the probe makes contact with the point of interest. The relative location of the probe and the object indicates the height of the object at the point of interest. Proceeding in this manner over all points of interest allows the surface representation of the object to be generated. Capacitance probes, as well as air nozzles that allow back-pressure detection, may also be employed in a similar fashion, as they may be used to detect when contact has been made with the point of interest on the object.

Returning to FIG. 3, controller 340 controls the operation of manipulator 320 so that the portion of the object to be inspected lies within the focal plane of imaging chain 310. Controller 340 performs this function by using the surface representation that is generated by surface mapping system 330 to determine the proper translational position and rotational orientation of the object so that the portion of the object to next be inspected may be imaged. A general-purpose algorithmic controller, such as a computer, or specialized hardware, may be employed for controller 340.

With respect to translation, controller 340 may use the surface representation is to position the portion of the object to be inspected within the field of view of imaging chain 310. Controller 340 does this by translating the object in a direction parallel to the focal plane of imaging chain 310. Also, controller 340 may use the surface representation to translate the object under inspection in a direction perpendicular to the focal plane so that the portion to be inspected lies within the focal plane.

Figure 6:
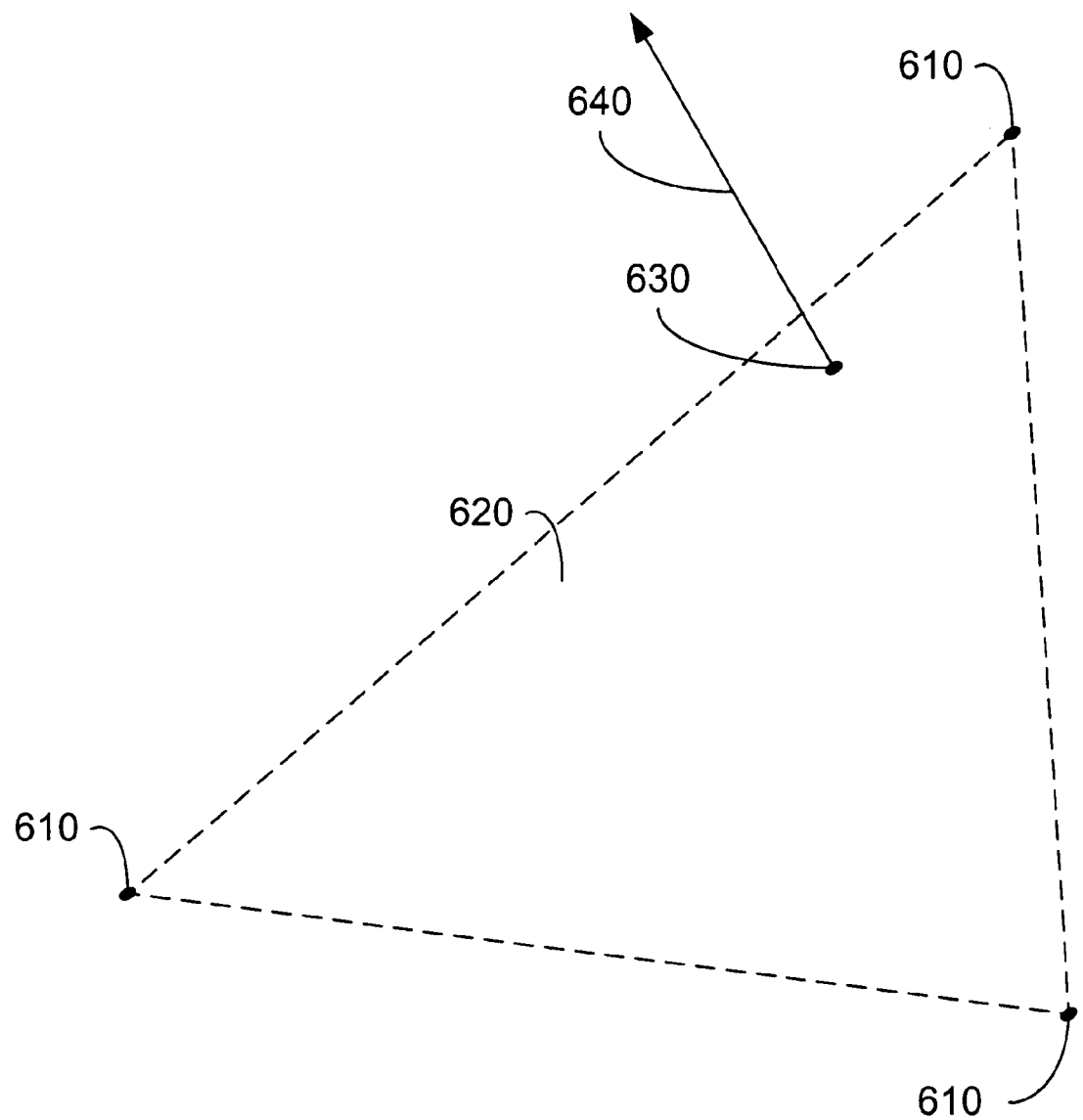
FIG. 6 is a simplified diagram depicting how information from a surface representation from the surface mapping system may be utilized by a controller to control a manipulator in an image-based inspection system according to an embodiment of the invention.

Controller 340 also controls the rotational orientation of the object by way of manipulator 320. The surface representation from surface mapping system 330, which provides the data that controller 340 utilizes to perform this function, may be utilized in a multitude of ways to accomplish this task. For example, as shown in FIG. 6, at least three points 610 on the surface of the object under inspection, as identified by surface mapping system 330, could be used to define a plane 620 in space. Points 610 reside near point of interest 630, representing the portion of the object to be inspected. Such a task is possible since any three points in space that do not describe a single line necessarily define a unique plane. Controller 340 then calculates a vector 640 normal to plane 620, and informs manipulator 320 to rotate the object so that vector 640 is perpendicular to the focal plane of imaging chain 310 while preventing point of interest 630 from translating substantially. As a result, the maximum amount of the portion of the object to be inspected will lie within the focal plane.

Alternately, controller 340 may generate such a vector by calculating a smooth curved surface described by a plurality of identified points from the surface representation that reside near the portion of the object to be inspected. Controller 340 would then use that vector in the same way as described above to control manipulator 320. Myriad other methods of using identified points from the surface representation that reside near the portion of the object to be inspected may be employed by controller 340 to properly position the object under inspection.

In order to control manipulator 320 accurately, controller 340 may require positioning feedback from manipulator 320 to precisely determine the position and orientation of the object under inspection. Alternately, such feedback may not be necessary if manipulator 320 itself positions the object under inspection accurately based on the control provided by controller 340.

Controller 340 may also control the operation of the remaining portions of inspection system 300, as centralized control of the various elements shown in FIG. 3 may be desirable over a systems that relies on each of the elements being self-controlling.

Returning once more to FIG. 3, the components thus far described (imaging chain 310, manipulator 320, surface mapping system 330, and controller 340), provide an image-based inspection system capable of allowing a user to determine the status or quality of the object under inspection, assuming the user can view the images captured by imaging chain 310. Alternately, an interpreter 350 may be employed to automatically interpret the images captured by imaging chain 310 to determine the status or quality of the object under inspection. A general-purpose algorithmic controller, such as a computer executing software appropriate to determine the status of the object, may serve as interpreter 350. Otherwise, specialized hardware performing the same task may also be employed in the same capacity. Alternately, controller 340 may perform the functions described above for interpreter 350.

Figure 7:
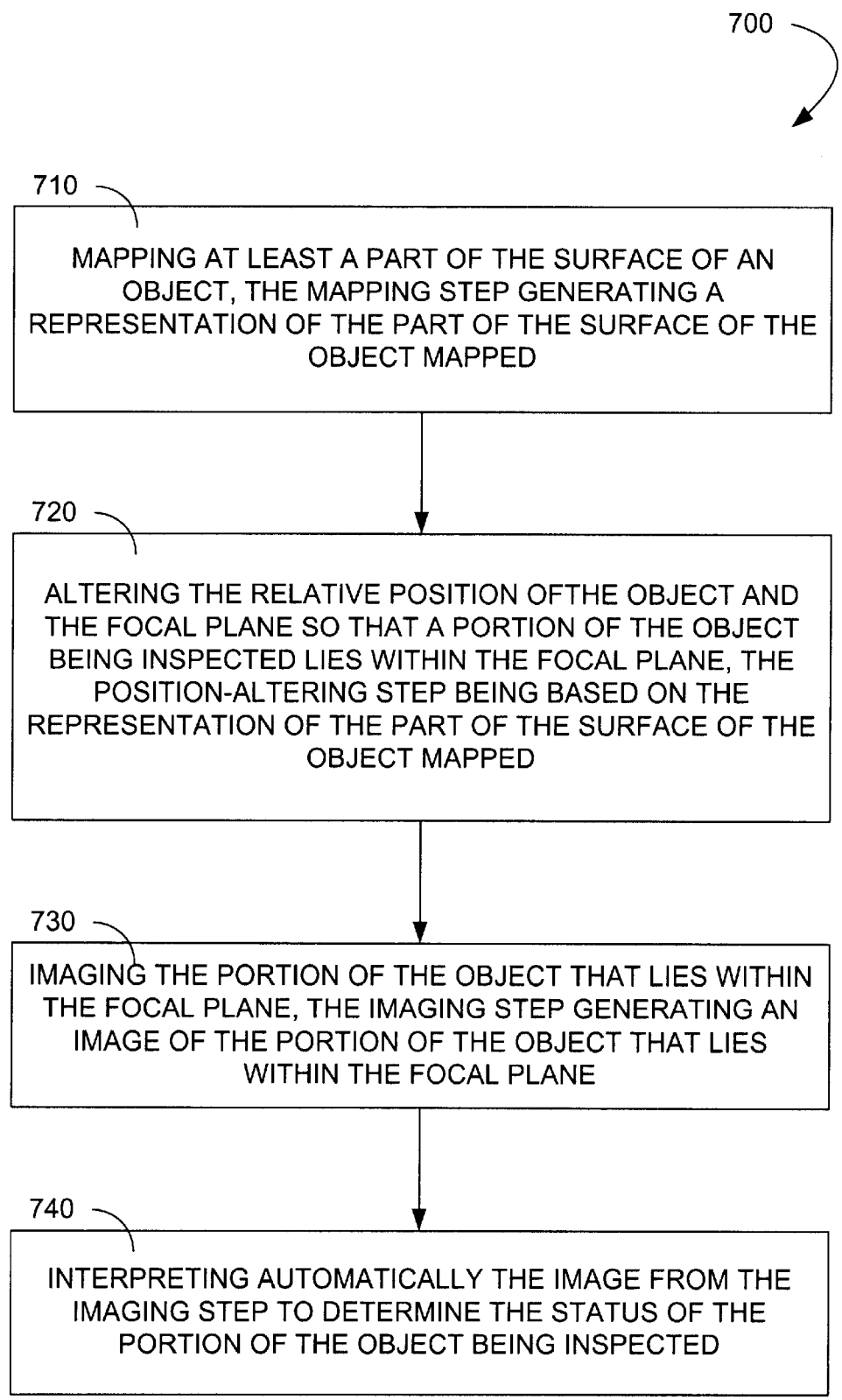
FIG. 7 is a flowchart of a method of image-based inspection according to an embodiment of the invention.

An embodiment of the present invention can also be described as a method 700 (from FIG. 7) of image-based inspection of an object. Method 700, as shown in FIG. 7, utilizes any image-based technology, including, but not limited to, optical- or x-ray-based detection, that defines a focal plane. First, a part of the surface of the object to be inspected is mapped (step 710). This mapping step generates a representation of the part of the surface of the object that was mapped. The translational position and rotational orientation of the object or the focal plane is then altered using the surface representation from the mapping step so that a portion of the object being inspected lies within the focal plane (step 720). Finally, the portion of the object that lies within the focal plane is imaged (step 730), with the imaging step generating an image of the portion of the object being inspected. In some embodiments, the image generated by the imaging step may be inspected manually to determine the status or quality of the portion of the object being inspected. Alternately, the method of inspection may interpret the image automatically to determine the status or quality of that portion of the object (step 740). Furthermore, the position-altering, imaging, and interpreting steps may be repeated for each additional portion of the object to be inspected.

From the foregoing, the embodiments of the invention discussed above have been shown to provide an image-based inspection system which allows relative translational and rotational movement between a focal plane of an image-based inspection system and an object under inspection. In addition, other specific systems and methods embodying the invention are also possible. Therefore, the present invention is not to be limited to the specific forms so described and illustrated; the invention is limited only by the claims.

What is claimed is:

1. An image-based inspection system for inspecting an object, comprising:

means for imaging a portion of the object, the imaging means defining a focal plane in which the portion of the object must be positioned in order to be imaged by the imaging means, the imaging means generating an image of the portion of the object;

means for altering the translational and orientational position of the object to be inspected relative to the focal plane;

means for mapping at least a part of the surface of the object, the mapping means generating a representation of the part of the surface of the object; and means for controlling the operation of the position-altering means using the representation of the part of the surface of the object so that the portion of the object being inspected lies substantially within the focal plane.

2. The image-based inspection system of claim 1, wherein the position-altering means comprises means for manipulating the translational and rotational position of the object to be inspected.

3. The image-based inspection system of claim 1, wherein the position-altering means comprises means for manipulating the translational and rotational position of the imaging means.

4. The image-based inspection system of claim 1, further comprising means for automatically interpreting the image from the imaging means to determine the status of the portion of the object being inspected.

5. An image-based inspection system for inspecting an object, comprising:

an imaging chain configured to generate an image of a portion of the object, the imaging chain defining a focal plane in which the portion of the object must be positioned in order to be imaged by the imaging chain;

a manipulator configured to alter the translational and rotational position of the object being inspected relative to the focal plane;

a surface mapping system configured to map at least part of the surface of the object, the surface mapping system generating a representation of the part of the surface of the object; and a controller configured to control the operation of the manipulator using the representation of the part of the surface of the object so that the portion of the object being inspected lies substantially within the focal plane.

6. The image-based inspection system of claim 5, wherein the imaging chain comprises an optical-based imaging chain.

7. The image-based inspection system of claim 5, wherein the imaging chain comprises an ultraviolet-radiation-based imaging chain.

8. The image-based inspection system of claim 5, wherein the imaging chain comprises an infrared-based imaging chain.

9. The image-based inspection system of claim 5, wherein the imaging chain comprises a gamma-ray-based imaging chain.

10. The image-based inspection system of claim 5, wherein the imaging chain comprises an x-ray-based imaging chain.

11. The image-based inspection system of claim 10, wherein the x-ray-based imaging chain comprises a digital tomosynthesis imaging system.

12. The image-based inspection system of claim 10, wherein the x-ray-based imaging chain comprises an x-ray laminography imaging chain.

13. The image-based inspection system of claim 12, wherein the x-ray laminography imaging chain scans the object in a linear manner.

14. The image-based inspection system of claim 12, wherein the x-ray laminography imaging chain scans the object in a rotational manner.

15. The image-based inspection system of claim 14, wherein the x-ray laminography imaging chain comprises:

a rotary scanning x-ray tube configured to source the x-rays; and a rotary scintillator and camera configured to detect the x-rays from the scanning x-ray tube.

16. The image-based inspection system of claim 5, wherein the manipulator is configured to translate and rotate the object.

17. The image-based inspection system of claim 5, wherein the manipulator is configured to translate and rotate the imaging chain.

18. The image-based inspection system of claim 5, wherein the manipulator comprises a hexapod.

19. The image-based inspection system of claim 5, wherein the manipulator comprises an adjustment mechanism configured to provide translation of the object along any of three orthogonal axes, as well as rotation of the object about any two orthogonal axes parallel to the focal plane.

20. The image-based inspection system of claim 5, wherein the manipulator comprises an adjustment mechanism configured to provide translation of the object along any of three orthogonal axes, as well as rotation of the object about an axis parallel to the focal plane, and about an axis normal to the focal plane.

21. The image-based inspection system of claim 5, wherein the manipulator comprises an adjustment mechanism configured to provide translation of the object along any of three orthogonal axes, as well as rotation of the object about an axis parallel to the focal plane.

22. The image-based inspection system of claim 5, wherein the surface mapping system comprises a laser distance sensing system.

23. The image-based inspection system of claim 5, wherein the surface mapping system comprises a photogrammetry system.

24. The image-based inspection system of claim 5, wherein the surface mapping system comprises a physical probing system.

25. The image-based inspection system of claim 5, wherein the surface mapping system comprises a focus mapping system.

26. The image-based inspection system of claim 5, wherein the controller comprises a computer configured to generate a vector normal to the portion of the object being inspected based on the plane described by at least three nearby points on the surface of the object identified by the surface mapping system.

27. The image-based inspection system of claim 5, wherein the controller comprises a computer configured to generate a vector normal to the portion of the object being inspected based on a smooth curved surface described by a plurality of nearby points on the surface of the object identified by the surface mapping system.

28. The image-based inspection system of claim 5, further comprising an interpreter configured to automatically interpret the image from the imaging chain to determine the status of the object being inspected.

29. The image-based inspection system of claim 28, wherein the interpreter comprises a computer configured to interpret the image generated by the imaging chain.

30. A method of image-based inspection of an object, a portion of the object to be inspected being required to lie within a focal plane in order to be imaged, the method comprising:

mapping at least a part of the surface of the object, the mapping step generating a representation of the part of the surface of the object mapped;

altering the translational and rotational position of the object being inspected relative to the focal plane so that the portion of the object being inspected lies within the focal plane, the position-altering step being based on the representation of the part of the surface of the object mapped; and imaging the portion of the object that lies within the focal plane, the imaging step generating an image of the portion of the object being inspected.

31. The method of claim 30, wherein the position-altering step comprises manipulating the translational and rotational position of the object.

32. The method of claim 30, wherein the position-altering step comprises manipulating the translational and rotational position of the focal plane.

33. The method of claim 30, further comprising interpreting automatically the image from the imaging step to determine the status of the portion of the object being inspected.

* * * * *